US007722526B2

(12) United States Patent
Kim

(10) Patent No.: US 7,722,526 B2
(45) Date of Patent: May 25, 2010

(54) SYSTEM, METHOD AND APPARATUS FOR PREVENTING MOTION SICKNESS

(76) Inventor: Samuel Kim, 47 Roberts Rd., Englewood Cliffs, NJ (US) 07632

( * ) Notice: Subject to any disclaimer, the term of this patent is extended or adjusted under 35 U.S.C. 154(b) by 0 days.

(21) Appl. No.: 11/166,483

(22) Filed: Jun. 24, 2005

(65) Prior Publication Data

US 2006/0015000 A1  Jan. 19, 2006

Related U.S. Application Data

(60) Provisional application No. 60/588,710, filed on Jul. 16, 2004, provisional application No. 60/630,055, filed on Nov. 22, 2004.

(51) Int. Cl.
*A61M 21/00* (2006.01)
(52) U.S. Cl. ...................................................... 600/27
(58) Field of Classification Search ............. 600/26–28; 702/150; 345/649, 619, 656
See application file for complete search history.

(56) References Cited

U.S. PATENT DOCUMENTS

| | | | |
|---|---|---|---|
| 2,334,018 A | | 11/1943 | Mayne |
| 4,929,228 A | | 5/1990 | Hendricks |
| 4,930,435 A | | 6/1990 | Newman |
| 5,067,941 A | * | 11/1991 | Hendricks ..................... 600/27 |
| 5,161,196 A | | 11/1992 | Ferguson |
| 5,647,835 A | | 7/1997 | Martineau |
| 5,966,680 A | | 10/1999 | Butnaru |
| 6,042,533 A | | 3/2000 | Kania |
| 6,228,021 B1 | | 5/2001 | Kania |
| 6,275,998 B1 | | 8/2001 | Tromble |
| 6,443,913 B1 | * | 9/2002 | Kania .......................... 600/595 |
| 6,497,649 B2 | | 12/2002 | Parker et al. |
| 6,663,155 B1 | | 12/2003 | Malone et al. |
| 6,692,428 B1 | | 2/2004 | Kania |
| 6,719,343 B2 | | 4/2004 | Emerling et al. |
| 6,866,225 B2 | | 3/2005 | Jones et al. |
| 7,046,259 B2 | | 5/2006 | Humphries |
| 2001/0000459 A1 | | 4/2001 | Kania |
| 2002/0163215 A1 | | 11/2002 | Emerling et al. |
| 2004/0090525 A1 | * | 5/2004 | Eichmann ................... 348/148 |
| 2004/0217234 A1 | * | 11/2004 | Jones et al. .............. 244/118.5 |
| 2004/0217976 A1 | | 11/2004 | Sanford |
| 2004/0217978 A1 | * | 11/2004 | Humphries ................. 345/649 |

OTHER PUBLICATIONS

Michael J. Griffen and Maria M. Newman, "Visual Field Effects on Motion Sickness in Cars", Aviation, Space, and Environmental Medicine, Sep. 2004, vol. 75, No. 9.
Patricia M. Bercham, "Motion Sickness Literature Search", Army Research Laboratory, ARL-MR-504, May 2002.

* cited by examiner

*Primary Examiner*—Charles A Marmor, II
*Assistant Examiner*—Christine D Hopkins
(74) *Attorney, Agent, or Firm*—Bergman & Song LLP; Michael Bergman

(57) ABSTRACT

A system, method and apparatus for preventing motion sickness from afflicting a passenger in a moving vehicle which includes a means for capturing and substantially simultaneously displaying video images collected from a frontal view to a passenger having an obstructed view of the environment in front of the moving vehicle. The system, method and apparatus includes cropping/zooming the video images displayed to the passenger in order to create a view for the passenger in order to prevent motion sickness from afflicting the passenger.

21 Claims, 6 Drawing Sheets

1A

1B - Zoom

1C - Non-Centered Crop and Enlarge

1A

1B - Zoom

1C - Non-Centered Crop and Enlarge

2A

2B - Text or Images Over Video

2C - Video in Computer Window

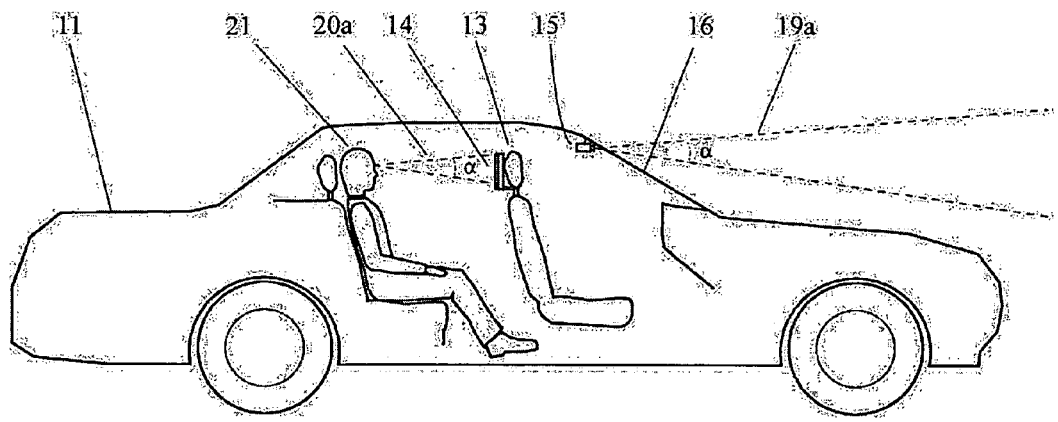
3A
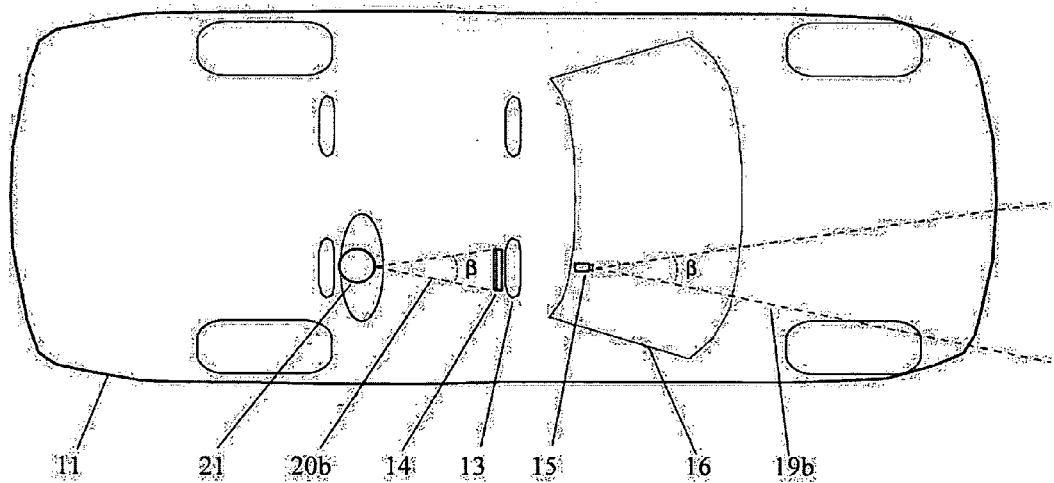
3B
FIGURE 3 - System of Preventing Motion Sickness

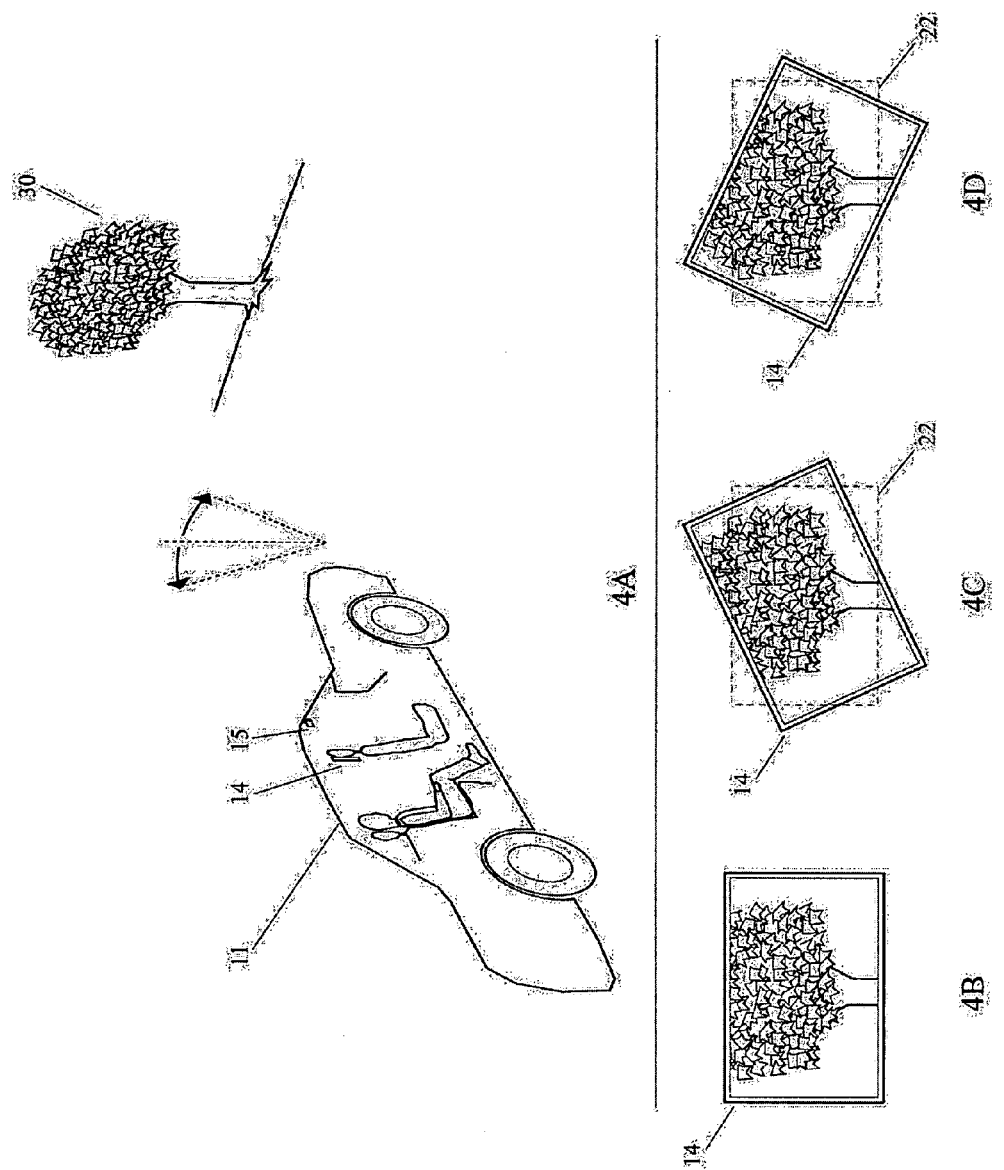
FIGURE 4 - Stationary Point of Reference in ROLL

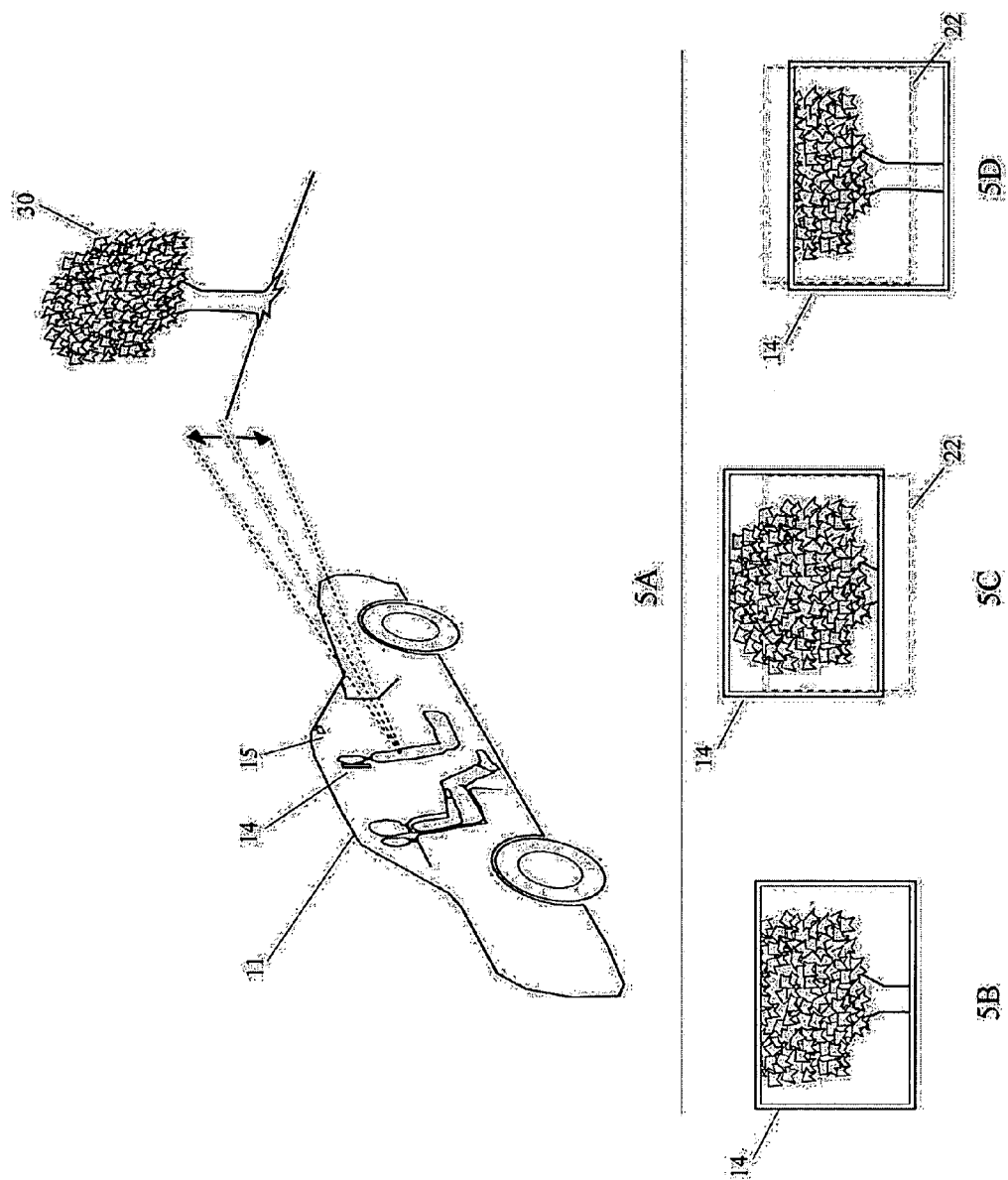
FIGURE 5 - Stationary Point of Reference in PITCH

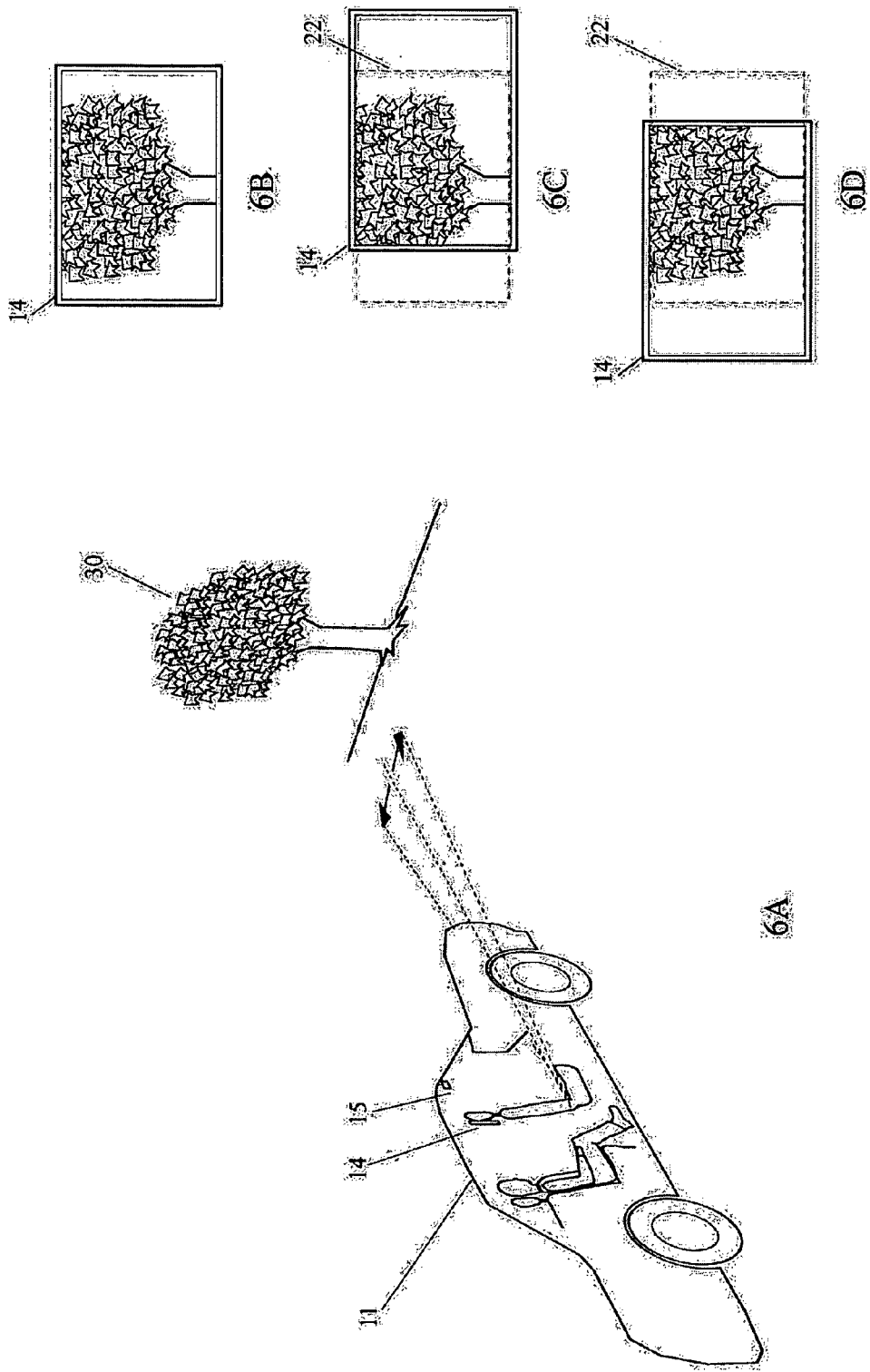
FIGURE 6 - Stationary Point of Reference in YAW

SYSTEM, METHOD AND APPARATUS FOR PREVENTING MOTION SICKNESS

CROSS-REFERENCE TO RELATED APPLICATIONS

This application relates to and claims the benefit of U.S. Provisional Patent Application Ser. No. 60/588,710, entitled, "METHOD OF PREVENTING MOTION SICKNESS", filed Jul. 16, 2004, which co-pending application is hereby incorporated by reference in its entirety.

This application is also related to and claims the benefit of co-pending U.S. Provisional Patent Application Ser. No. 60/630,055, entitled, "METHOD OF PREVENTING MOTION SICKNESS WHILE READING TEXT OR VIEWING AN IMAGE", filed Nov. 22, 2004, which co-pending application is hereby incorporated by reference in its entirety.

BACKGROUND OF THE INVENTION

The present invention relates generally to a system, method and apparatus for preventing motion sickness. More specifically the present invention relates to a system, method and apparatus for preventing motion sickness of a passenger traveling in a moving vehicle such as an automobile, boat, train, or an airplane.

Motion sickness relates to the sense of balance, equilibrium and spatial orientation. The sense of balance is controlled and maintained by intricate interaction of multiple parts of the human body, specifically, the inner ears (also called the labyrinth), the eyes, skin pressure receptors, muscle and joint sensory receptors, and the central nervous system. The inner ears monitor motion, such as turning and tilting. The eyes monitor where the body is in space (i.e. upside down, right side up, etc.) and also directions of motion. The skin pressure receptors, such as in the joints and spine, determine what part of the body is down and touching the ground or other surfaces. The muscle and joint sensory receptors determine which parts of the body are moving. The central nervous system (the brain and spinal cord), processes all of the information from the four other systems to determine the spatial orientation and motion of the body.

People may be afflicted with motion sickness when the central nervous system receives conflicting messages from the other four systems. For example, an automobile passenger sitting in the rear seat of a moving car typically has a limited view of the road ahead of the car. The passenger's inner ears and skin receptors may detect the motion of travel however, the passenger's eyes cannot properly perceive the motion because of the obstructed view of the road ahead. As such the passenger's central nervous system receives conflicting messages regarding the passenger's motion, causing motion sickness.

In another example, a passenger in a train, airplane or boat may sense or feel relative motion, e.g. tilting left or right, but if there is no external stationary point of reference, such as the horizon or a tree, due to a lack of windows, the passenger will not be able to visually detect his or her own relative motion, and this may trigger motion sickness. Further, it has also been found that virtual reality simulators can cause motion sickness in certain people. In contrast to moving vehicles, in some virtual reality simulators, the user views the environment portrayed by the simulator as in motion while sitting in a seat that remains fixed. The inner ears do not sense the same motion and hence a conflicting message is received in the central nervous system. In other virtual reality simulators, the user wears a head-mounted display, essentially a helmet with a screen placed in front of the eyes. A computer uses a motion detector in the helmet to determine the orientation of the user's head and thus, what to display on the screen. Because of a slight time lag involved in detecting motion and in rendering the graphics, what the user sees does not always precisely match the motion of the user's head (or inner ears), often causing motion sickness.

Additionally, people having inner ear damage from a head injury or an infection can also be afflicted with motion sickness. A damaged inner ear does not send the same signals as a healthy inner ear. The conflicting signals regarding the sensation of motion and/or rotation may cause motion sickness.

It has been found that motion sickness affects a large number people, including children, who are not legally allowed to sit in the front seat of an automobile where the likelihood of being afflicted with motion sickness is lower. The symptoms of motion sickness can include a general feeling of being unwell (malaise), nausea or vomiting, or both, headaches, cold sweating and a pale appearance. Symptoms may alleviate when the motion stops; however, it has been found that for some people it can take a significant period of time for symptoms to subside. A particularly susceptible person may become used to the motion during extended trips, such as on a long car trip or cruise. However, it has been found that even though the symptoms may subside during the trip, when the trip ends, symptoms can reoccur.

There have been many attempts to prevent or alleviate the effects of motion sickness. One well known method is for a passenger traveling in a moving vehicle to look outside the moving vehicle at objects that are stationery. This allows the passenger to visually perceive his or her own relative motion and determine spatial orientation, hence preventing motion sickness.

It has been found that automobile drivers rarely are afflicted with motion sickness. This may be a result of the driver's continued concentration on driving the vehicle in order to properly navigate and traverse the road in a safe manner. The unintended benefit of the driver's concentration is to constantly perceive his or her own motion relative to the environment outside the automobile. Because the natural tendency for many passengers is to look forward, rather than out a side window, passengers in the rear seat of the automobile where the view of the road ahead is obstructed may get sick. Moreover, in today's automobiles, third row seating is commonplace, providing seating for passengers further back in the automobile where the view of the road ahead is even more obstructed. Additionally, vans and buses alike may have even more seating with obstructed and limited views of the road ahead. The number of potential persons afflicted with motion sickness grows with the amount of rows in any vehicle, including boats, trains and airplanes, where the passengers are even more removed from the view in front or outside of the vehicle.

Boaters often prevent the onset of motion sickness by focusing on a fixed object on land, such as a dock or a building. In open water it has been found that sea-sickness may be alleviated by focusing on the horizon, which is perceived as a fixed object to the boater on the deck of a boat. However, as in an airplane, and similar to passengers in the rear seat of a car, passengers traveling in the cabin of a boat have limited viewable area and may not be able to look upon fixed objects or the horizon.

There have been many attempts to prevent motion sickness that are the subject of the U.S. patents. For example, U.S. Pat. No. 6,692,428 to Kania discloses an apparatus having a sensor that detects a motion of an object and a sensory converter which converts the detected motion to corresponding sensory signals, which can be audio, white noise or video. The sensory signals are designed to alleviate motion signals by using varying audio frequencies and/or colors displayed to the user selected in proportion to the determined motion. In addition, U.S. Pat. No. 6,497,649 to Parker, et al., discloses displaying an independent visual background via a head-mounted display with a visual reference corresponding to the perceptions of a person's vestibular system. Another attempt to prevent motion sickness is disclosed in U.S. Pat. No. 6,275,998 to Tromble which shows a vision occluding eye shield which completely blocks the peripheral vision of the wearer to the discernment of motion and which blocks most or all of the superior field of vision of the wearer. When worn by a passenger the device blocks perception of objects passing through the peripheral field of vision in the side windows and through the front window, while allowing the wearer to focus on tasks or objects within the vehicle by looking through the unoccluded portion.

The drawback of Kania and Parker is that they require the use of motion sensors, which can introduce a perceptible delay, which in turn, could render the device ineffective.

The drawback of Parker and Tromble, inter alia, is that they are intrusive as devices need to be worn by the user. As such, there exists a need for a system and method of preventing motion sickness that is not intrusive to the user.

There have also been many attempts to treat motion sickness medically, with pharmaceutical solutions and other medicinal treatments. Some preventative medications can be purchased without a prescription (e.g., Dramamine®, Bonine®, Marezine®). Stronger medicines such as tranquilizers and nervous system depressants usually require a prescription. The downside of using any of these medications includes the cost, the inconvenience, and the potential side effects.

Other medical solutions involve the use of magnetic or metallic bracelets and/or jewelry. Some jewelry is worn on pressure points in an attempt to alleviate motion sickness. It has been found however, that such devices have limited success in preventing motion sickness. As such there exists a need for an effective system and method for preventing motion sickness without using medications or medical devices.

The afore-mentioned problems, drawbacks, and disadvantages, in addition to others, are alleviated by the present invention disclosed herein where an object thereof is to provide a non-intrusive, non-medicinal, safe and effective system, method and apparatus for preventing motion sickness.

SUMMARY OF THE INVENTION

The present invention includes a system, method and apparatus for preventing motion sickness using a video camera and a video display, with a substantially real-time video feed. An object of the present invention is to provide a rear seat passenger in a vehicle with a view of an external, stationary point of reference via the display, as if there were a window directly in front of the passenger.

In a first aspect, the present invention may include an apparatus for preventing motion sickness from afflicting a passenger in a moving vehicle, the apparatus including a video camera connected to the vehicle, where the camera is structured and arranged to capture images from the front of the vehicle; and a means for displaying images captured by the camera to the passenger, where the images are displayed substantially simultaneously with the capture of the images and where the images are displayed in a form and manner to create a view forward of the vehicle for the passenger in order to prevent motion sickness from afflicting the passenger. The present invention may also include a means for adjusting the images, which may include cropping, resizing, and repositioning the images, a means for enhancing or modifying the images. The present invention may also include means for adjusting the camera, including zoom, angle, light sensitivity, and position. The means for adjusting the images and the means for adjusting the camera may be set to predetermined settings.

The camera has a first field of view, which may be defined by a cropped image presented in the means for displaying images, where the display may be positioned substantially in front of the passenger having a second field of view. The second field of view may be defined by the passenger's view of the cropped image. The first and second fields of view may have substantially the same angle.

In some embodiments, the means for displaying images further include a means for displaying text, or other images, superimposed over the displayed video images. In still other embodiments the video images may be shown in the display combined with the video output of a computer or other video device.

In a second aspect, the present invention may include a system for preventing motion sickness from afflicting a passenger in a moving vehicle, where the system includes a camera attached to the vehicle and the camera is positioned to have a first field of view substantially in front of the vehicle. The present invention in this embodiment also includes a display fixed to the vehicle and in communication with the camera where the display displays images captured and substantially simultaneously transmitted by the camera. The images relay motion of the vehicle relative to its environment from the perspective of the moving vehicle such that a passenger seated within the vehicle may view the displayed images in order to prevent motion sickness. The display may be positioned substantially in front of the passenger having a second field of view, which may be defined by the passenger's view of the displayed image. The first field of view and the second field of view may have substantially the same angle. In some embodiments the camera may be electronically linked to the display. In still other embodiments the images are transmitted from the camera to the display via wireless signal.

In a third aspect, the present invention includes a method for preventing motion sickness from afflicting a passenger of a moving vehicle, where the method includes the steps of displaying the motion of the vehicle to the passenger relative to the environment of the vehicle, where the displaying step comprises the steps of capturing the motion of the vehicle from the perspective of a forward looking unobstructed view, and substantially simultaneously transmitting the captured motion of the vehicle to a display positioned substantially directly in front of the passenger such that the passenger can view the displayed motion of the vehicle substantially simultaneously in order to prevent motion sickness from afflicting the passenger.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures, wherein:

FIG. 3A is a side view showing the instant application as applied to an automobile according to one embodiment of the invention;

FIG. 3B shows a top view of the instant application as applied to an automobile according to one embodiment of the invention;

FIGS. 4A-4D show the visual effect of an automobile rolling;

FIGS. 5A-5D show the visual effect of an automobile pitching; and

FIGS. 6A-6D show the visual effect of an automobile yawing.

DETAILED DESCRIPTION OF THE PREFERRED EMBODIMENTS

The present invention will now be described more fully with reference to the figures in which embodiments of the present invention are shown. It is important to note that the present invention may, however, be embodied in many different forms and should not be construed as being limited to the embodiments set forth herein.

The invention more fully described below provides an effective and non-intrusive system and method of preventing motion sickness. While the invention is disclosed and described in the figures with reference to an automobile, those skilled in the art will understand that the invention is equally applicable in other moving environments as well, such as, without limitation, a boat, train, airplane, space craft, and various amusement rides including a roller coaster.

Figure 1:
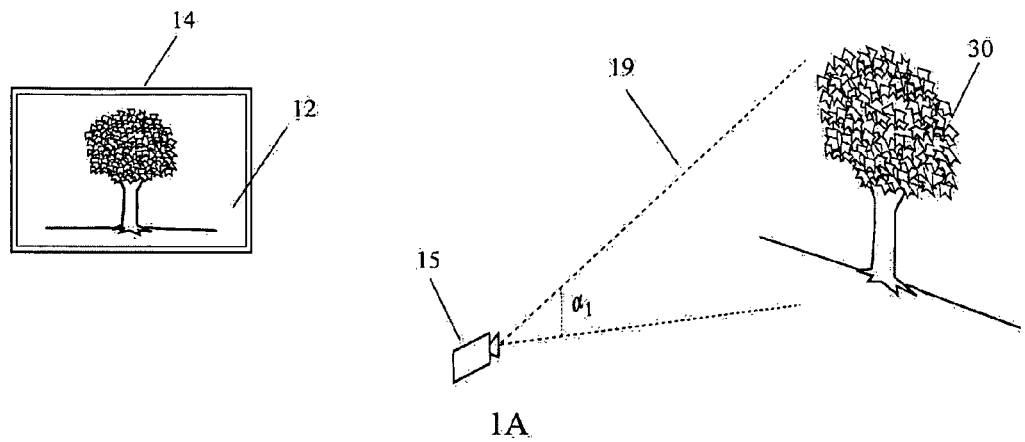
FIGS. 1A-1C show the use of a video camera and display.
Figure 1:
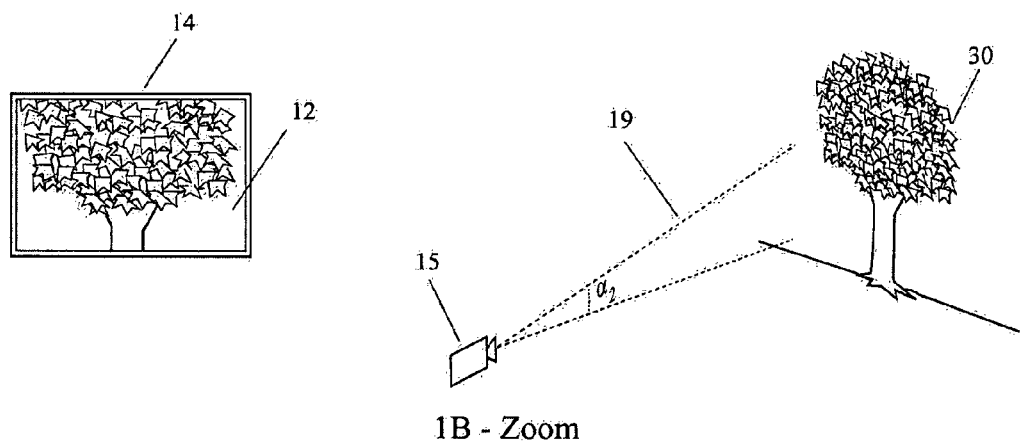
Figure 1:

In FIG. 1A, a video camera 15 is aimed at a tree 30, and a live video image 12 is transmitted and displayed in a video monitor 14. The live video image 12 may be transmitted by wire or wirelessly to monitor 14. The video camera 15's "field of view" 19 is defined by the image 12 displayed in monitor 14. The angle of vertical field of view 19 is $\alpha_1$.

In FIG. 1B, the live video image 12 is zoomed. This can be accomplished optically, by adjusting the positions of the lenses (not shown) in video camera 15, or digitally, by cropping and enlarging the live video image 12. The angle of vertical field of view 4 after zooming (whether optically or digitally) is $\alpha_2$, which is less than $\alpha_1$.

FIG. 1C shows an example of cropping and enlarging a subset image 24 that is not concentric with original video camera image 25. Image 24 is cropped and enlarged to fit monitor 14.

Figure 2:
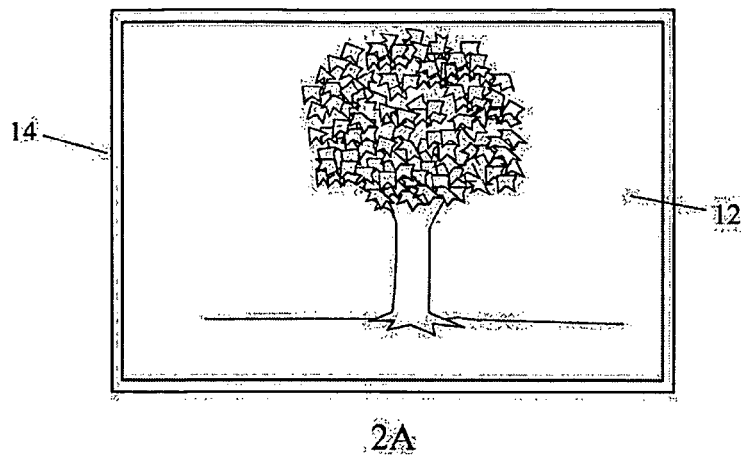
FIGS. 2A-2C show several embodiments of the invention.
Figure 2:
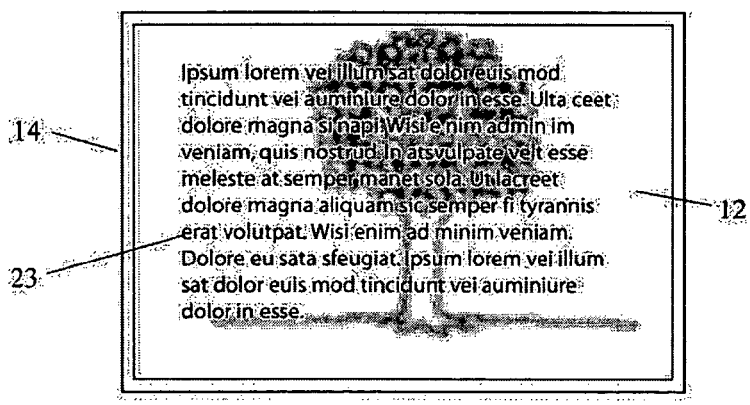
Figure 2:
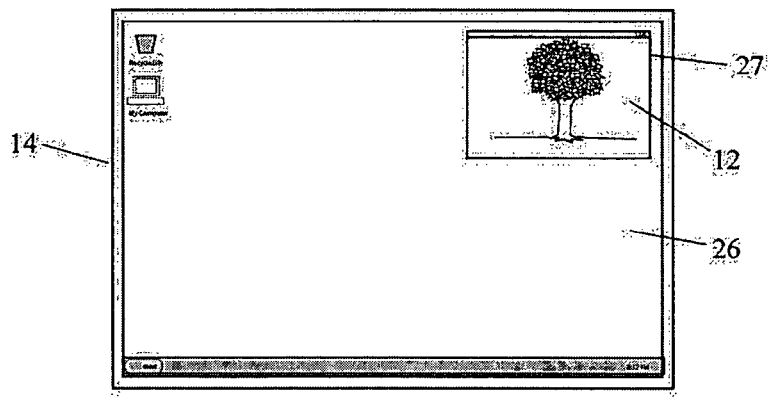

FIG. 2A shows monitor 14 displaying live video image 12. In FIG. 2B, text 23 is superimposed on the monitor 14, and image 12 is modified so that it does not interfere with the legibility of text 23. This modification may include, but is not limited to, blurring, and adjustment to brightness, contrast, color, and saturation. The color, font, and format of the text is also adjustable. Note that an image, such as a map (not shown), can also be superimposed on the monitor in place of, or in addition to, the text.

The text or image (such as a map) may also be displayed adjacent to the video image. In FIG. 2C, live video image 12 is displayed in a window 27 occupying a subset of monitor 14, which also displays an output 26 of a computer (not shown).

Referring now to FIGS. 3A and 3B, a system for preventing motion sickness is shown in connection with an automobile 11 carrying passenger 21. Video camera 15 may be mounted in a fixed position and aimed forward on the interior of windshield 16 of automobile 11. In some embodiments camera 15 may be mounted on an external position of automobile 11. This system is also effective with the use of multiple cameras (not shown) capturing views from different angles and feeding multiple monitors.

A passenger 21 may be sitting in the left, right or even the center rear seat. Regardless of which rear seat passenger 21 occupies, the view of passenger 21 will likely be partially obstructed by another seat or passenger. It has been found that rear seat passengers are more likely to be afflicted with motion sickness because they lack an unobstructed view of the outside. If passenger 21 only looks forward, he or she may not see an external, stationary reference point while still sensing his or her own motion. This may create conflicting messages in the central nervous system of passenger 21 and can lead to motion sickness.

In order to prevent such motion sickness, the present invention includes video monitor 14 which may be mounted directly in a view (20a and 20b) of passenger 21. The monitor 14 can be mounted on a headrest 12 of a front seat, or anywhere else in the car, including between the front seats and from the ceiling. The position of monitor 14 is adjustable, and ideally, it should be positioned at the eye-level of passenger 21. A continuous, live video image is transmitted from the video camera 15 to the video monitor 14 by wire (not shown) or in some embodiments, wirelessly.

In the preferred embodiment the video images captured in video camera 15 are displayed substantially simultaneously in order to create a "real-time" view for passenger 21 via monitor 14. Passenger 21 preferably will be able to visually perceive his or her own motion relative to an external stationary reference point via the monitor 14 in concert with the motion he or she senses via the vestibular senses in the inner ears. Hence, the central nervous system of passenger 21 does not receive conflicting messages regarding the passenger's spatial orientation and the passenger will not be afflicted with motion sickness.

However, it will be understood that in some applications, for example in a multiple-car vehicle (not shown) such as a train, a monitor will display images captured by the video camera with a precisely-controlled delay. In this scenario, video images captured by a video camera attached to the first car would be displayed in a monitor attached to another car at the moment when that other car reaches the position and orientation the first car was in when the image was captured.

For best results, the fields of view 19a and 19b should be adjusted (via optical zoom and/or digital zoom) to be substantially equal to the fields of view 20a and 20b respectively of passenger 21. The fields of view 20a and 20b depend upon the size of the monitor 14 and the distance between passenger 21 and monitor 14. The video camera 15 may have an "infrared mode" for operation at night.

Referring now to FIG. 4A, there is shown a view of relative motion of automobile 11 in roll. In this example, a fixed object, tree 30, is directly in front of automobile 11. In FIG. 4B, monitor 14 shows an initial video image of tree 30. When automobile 11 rolls (rotates around the forward-pointing axis) as depicted in FIG. 4A, the image displayed in monitor 14 will change. FIG. 4C shows that when automobile 11 rolls left, monitor 14 also rotates left. Because video camera 15 is mounted on automobile 11 and also rotates left, the image 12 of the tree 30 rotates right relative to the monitor the same amount. The result is that the image of the tree remains stable and upright relative to the original position 22 of the monitor. FIG. 4D shows a similar result when the automobile 11 rolls right. Like a window, monitor 14 provides an external, stationary point of reference even as the automobile 11 rolls.

Referring now to FIG. 5A, there is shown a view of relative motion of automobile 11 in pitch. Again, a fixed object, tree 30, is directly in front of automobile 11. In FIG. 5B, monitor 14 shows an initial video image of tree 30. When automobile 11 pitches (tilts forward and backward around the right-to-left axis) as depicted in FIG. 5A, the image displayed in monitor 14 will change. FIG. 5C shows that when automobile 11 pitches back (aiming the camera 15 higher), monitor 14 rises above its original position 22. Because video camera 15 is mounted on automobile 11 and aims higher, the image 12 of the tree 30 moves down relative to the monitor a similar amount. The result is that the image of the tree remains stable. FIG. 5D shows a similar result when the automobile 11 pitches forward. Like a window, monitor 14 provides a stationary point of reference even as the automobile 11 pitches.

Referring now to FIG. 6A, there is shown a view of relative motion of automobile 11 in yaw. Again, a fixed object, tree 30, is directly in front of automobile 11. In FIG. 6B, monitor 14 shows an initial video image of tree 30. When automobile 11 yaws (turns right or left around the vertical axis) as depicted in FIG. 6A, the image displayed in monitor 14 will change. FIG. 6C shows that when automobile 11 yaws right, monitor 14 moves right of its original position 22. Because video camera 15 is mounted on automobile 11 and aims to the right, the image 12 of the tree 30 moves left relative to the monitor a similar amount. The result is that the image of the tree remains stable. FIG. 5D shows a similar result when the automobile 11 yaws left. Like a window, monitor 14 provides a stationary point of reference even as the automobile 11 yaws.

It will be apparent to one of skill in the art that described herein is a novel system, method and apparatus for preventing motion sickness. While the invention has been described with reference to specific preferred embodiments, it is not limited to these embodiments. The invention may be modified or varied in many ways and such modifications and variations as would be obvious to one of skill in the art are within the scope and spirit of the invention and are included within the scope of the following claims.

What is claimed is:

1. An apparatus for preventing motion sickness from afflicting a passenger in a moving vehicle, the apparatus comprising:
    a video camera connected to the vehicle, said camera structured and arranged to capture images from the front of the vehicle, said camera having a camera field of view,
    a means for displaying images captured by said video camera to the passenger, where said images are displayed substantially simultaneously with the capture of the images and where said images are displayed in a form and manner to provide a view of external, stationary points of reference for the passenger in order to prevent motion sickness from afflicting the passenger, said means for displaying having a display field of view corresponding to its location with respect to said passenger, and
    means for adjusting said camera to produce a camera field of view in accordance with said display field of view.

2. The apparatus according to claim 1, where said means for displaying images further comprises a means for displaying graphics in association with the displayed video images.

3. A system for preventing motion sickness from afflicting a passenger in a moving vehicle, the system comprising:
    a video camera fixed to the vehicle, said camera positioned to have a first field of view substantially in front of the vehicle, and
    a display fixed to the vehicle and in communication with said camera, said display substantially simultaneously displaying images captured and transmitted by said camera, where said images show external, stationary points of reference, such that a passenger within said vehicle may view the displayed images in order to prevent motion sickness wherein said display is positioned substantially in front of the passenger having a second field of view of the displayed images and the first field of view and the second field of view have substantially the same angle.

4. The system according to claim 3, where said images are cropped, resized, and repositioned to predetermined specifications.

5. The system according to claim 4, where said camera is zoomed to a predetermined specification.

6. The system according to claim 5 further comprising graphics displayed in association with the displayed video images.

7. A method for preventing motion sickness from afflicting a passenger of a moving vehicle, the method comprising the steps of:
    displaying the motion of the vehicle to the passenger relative to the environment of the vehicle, where said displaying step comprises the steps of capturing the motion of the vehicle from the perspective of a forward looking unobstructed view having a particular capture viewing angle, and substantially simultaneously transmitting the captured motion of the vehicle to a display positioned substantially directly in front of the passenger such that the passenger can view the displayed motion of the vehicle over a display viewing angle substantially equal to said capture viewing angle substantially simultaneously in order to prevent motion sickness from afflicting the passenger.

8. The method according to claim 7 further comprising displaying graphics in association with the displayed motion of the vehicle.

9. A method of reducing vehicle occupant motion sickness comprising:
    forming an image signal representing an external environment with an image acquisition device;
    receiving said image signal at a display device;
    presenting an image on said display device, said image corresponding to said image signal; and
    adjusting said image acquisition device to equalize a field of view angle of said image acquisition device and a field of view angle of said display device.

10. A method of reducing vehicle occupant motion sickness as defined in claim 9 wherein said adjusting said image acquisition device comprises adjusting a zoom lens of said image acquisition device.

11. A method of reducing vehicle occupant motion sickness as defined in claim 9 wherein said adjusting said image acquisition device comprises adjusting a position of a lens of said image acquisition device with respect to a sensor device of said image acquisition device.

12. A method of reducing vehicle occupant motion sickness as defined in claim 9 wherein said image acquisition device comprises a digital video camera.

13. A method of reducing vehicle occupant motion sickness as defined in claim 9 wherein said adjusting said image acquisition device comprises adjusting a sensor device of said image acquisition device to provide a digital zoom function.

14. A motion sickness reduction device comprising:
    a user locating apparatus, said user locating apparatus being adapted to position an eye of a user in generally fixed spatial relation to said user locating apparatus;
    an image display device, said image display device being disposed in spatial relation to said user locating apparatus so as to maintain an average distance between said eye and said image display device, said average distance defining a user field of view angle in conjunction with a spatial dimension of said image display device;

a camera, said camera including a focusing device, said focusing device being adapted to define a camera field of view angle of said camera; and an adjusting device, said adjusting device being coupled to said focusing device and adapted to establish a relationship between said camera field of view and said user field of view.

15. A motion sickness reduction device as defined in claim 14 wherein said relationship between said camera field of view and said user field of view comprises an equality relationship such that the camera field of view is angularly equal to said user field of view.

16. A motion sickness reduction device as defined in claim 14 wherein said focusing device comprises a zoom lens.

17. A motion sickness reduction device as defined in claim 16 wherein said adjusting device is mechanically coupled to said zoom lens device.

18. A motion sickness reduction device as defined in claim 16 wherein said adjusting device is adapted to adjust a position of a lens of said zoom lens device.

19. A motion sickness reduction device as defined in claim 14 wherein said user locating apparatus comprises a vehicle seat.

20. A motion sickness reduction device as defined in claim 14 wherein said display device comprises a video monitor.

21. A motion sickness reduction device as defined in claim 14 wherein said image display device is adapted to display a first image of an environment of a vehicle and a second image, said second image being superimposed with said first image.

* * * * *